(12) United States Patent
Rosenblum

(10) Patent No.: US 6,558,369 B2
(45) Date of Patent: May 6, 2003

(54) MALE CATHETER SECURING DEVICE

(76) Inventor: Jeffrey Rosenblum, Medical Arts Building, 80 W. Welsh Pool Rd., Suite 100, Exton, PA (US) 19341

(*) Notice: Subject to any disclaimer, the term of this patent is extended or adjusted under 35 U.S.C. 154(b) by 0 days.

(21) Appl. No.: 09/908,412

(22) Filed: Jul. 18, 2001

(65) Prior Publication Data

US 2003/0018321 A1 Jan. 23, 2003

(51) Int. Cl.[7] .......................... A61M 27/00; A61F 5/44
(52) U.S. Cl. ................................. 604/544; 604/353
(58) Field of Search ........................ 604/346, 347, 604/349, 351, 352, 353, 544, 523, 327, 328, 350

(56) References Cited

U.S. PATENT DOCUMENTS

| | | | | | |
|---|---|---|---|---|---|
| 3,998,228 A | * | 12/1976 | Poidomani | ................. | 604/351 |
| 4,713,066 A | * | 12/1987 | Komis | ................. | 604/349 |
| 4,840,187 A | * | 6/1989 | Brazier | ................. | 128/844 |
| 4,895,140 A | * | 1/1990 | Bellak | ................. | 600/39 |
| 5,538,584 A | * | 7/1996 | Metz | ................. | 128/844 |
| 5,797,890 A | * | 8/1998 | Goulter et al. | ................. | 604/351 |

* cited by examiner

Primary Examiner—Weilun Lo
Assistant Examiner—C Lynne Anderson
(74) Attorney, Agent, or Firm—Paul & Paul

(57) ABSTRACT

The present invention is a male catheter securing device for use on male patients having a catheter inserted within their penis. The device is comprised of a cylindrical sleeve portion comprised of strands of non-elastic resilient material. Each end of the cylindrical sleeve portion has attachment means, which anchor the device so as cause elongation and therefore, constriction of the strands when transverse force is applied to the device.

13 Claims, 2 Drawing Sheets

MALE CATHETER SECURING DEVICE

BACKGROUND OF THE INVENTION

An indwelling urethral catheter is commonplace in hospitals, nursing homes, and various other patient environments. A catheter is a drainage tube placed through the urethra into the bladder. It is utilized for bladder drainage, urinary retention, post-surgery and numerous other scenarios. A catheter is maintained in position by an inflatable balloon at its tip within the urinary bladder of the patient.

Patients in whom these catheters are utilized may be elderly, debilitated, confused or combative. Hence, they may try to pull out the catheter with the inflatable balloon within the bladder resulting in the catheter trauma scenario. This causes prostate and urethra injury requiring immediate intervention; thereafter, pain and infection may ensue. Delayed stricture or scarring may result, also requiring operative means. These sequelae increase patient morbidity.

Most instruments which maintain a catheter in place, are based on taping or tying the instrument to the patient by conventional means, i.e. tape or string. These instruments have been ineffective based on their limited strength, discomfort and inability to accommodate movements of the patients.

A need exists for a simple inexpensive instrument that uses the movements of the patients to counteract removal of the catheter.

SUMMARY OF THE INVENTION

The Male Catheter Securing Device of the present invention secures a catheter to the patient's penis when force is applied to remove the device, preventing the aforementioned trauma. The more longitudinal force or force tending to remove the catheter that is applied to catheter, the tighter the catheter is maintained in position based on the device design. When the outward force is alleviated, so is the tightness with which the catheter is held in position.

The device is comprised of a cylindrical sleeve portion comprised of (preferably) helical strands or rushes. The device is secured to the body of the patient by variety of means including hook-and-pile fastener straps, belts and ties attached to the cylindrical sleeve portion. The helical strands are resilient and non-elastic and comprised of a number of materials, such as nylon, cotton, synthetic polymer or any other type of mill material that will accomplish the results set forth herein.

The device is attached to the patient by back loading the device over the penis with a catheter inserted therein. The hook-and-pile fastener strap or other type of strap, located at the base of the proximal end of the sleeve portion, produces a snug fit at the penile base. An adjustable belt is also located at the proximal end of the sleeve portion, configured to go around the patient's waist and under both legs for added security of the device. Ties are located at the distal (outer) end of the sleeve portion that are tied, taped or otherwise secured to or around the indwelling catheter.

The device functions similar to "Chinese handcuffs" or "finger-traps", wherein a finger is inserted into each end of the "Chinese handcuffs" and when pulled in opposite directions the cylinder would tighten; i.e. the diameter of the cylinder is reduced. Likewise, if the catheter is traumatically pulled, the device's diameter decreases, clamping down (constricting) on the penis, securing the catheter in position. Fundamentally, the strands which form the cylindrical sleeve portion invention are constricted when pulled. This keeps the catheter relatively immobilized, fixing it in position with regard to the urethra. Greater force to remove the invention further tightens the invention in position. Additionally, the device surrounds the penis, providing a cage effect, which protects the penis and tends to resist a patient from grasping the penis.

An object of the invention is to provide a device which will prevent trauma to the urinary tract of a patient.

Another object of the invention is to be economical and disposable.

These and other objects of the present invention will become more readily apparent when taken into consideration with the following descriptions and the attached drawings.

DETAILED DESCRIPTION OF THE DRAWINGS

Figure 1:
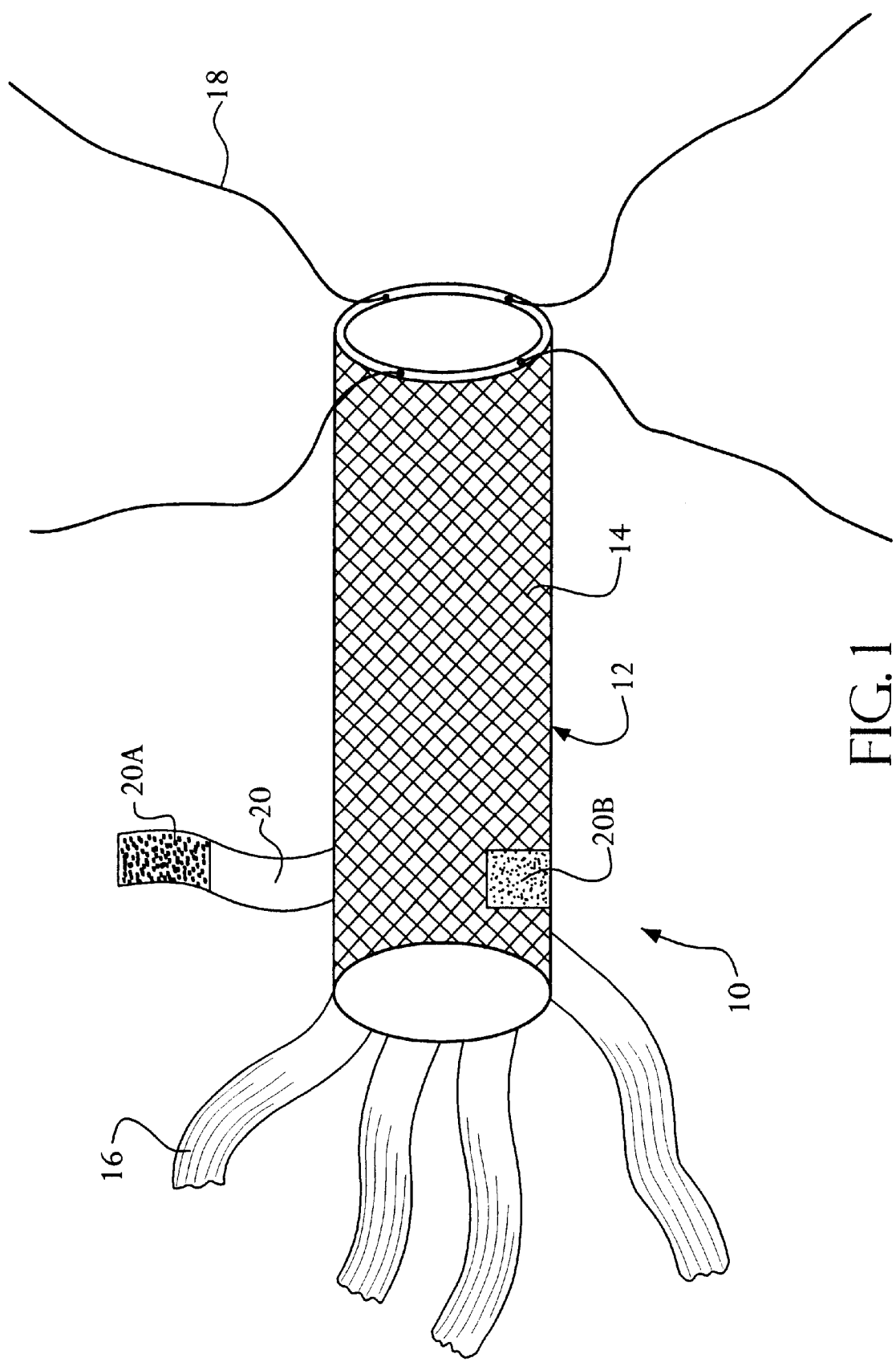
FIG. 1 is a perspective view of the device of the present invention prior to attachment to a patient.

Referring to the figures wherein like reference number correspond to like elements throughout the disclosure, there is shown in FIG. 1, a device 10 having a cylindrical sleeve portion 12 comprised of helical stands 14. The sleeve portion 12 has belts 16 with buckles 16A attached on a proximal end 12A and strings 18 on the distal end 12B. Additionally, on the proximal end 12A of the cylindrical sleeve portion 12, a hook-and-pile fastener strap 20 is positioned to produce a snug fit at the penile base when the unsecured fastener portion 20A engages the secured fastener portion 20B.

Figure 2:
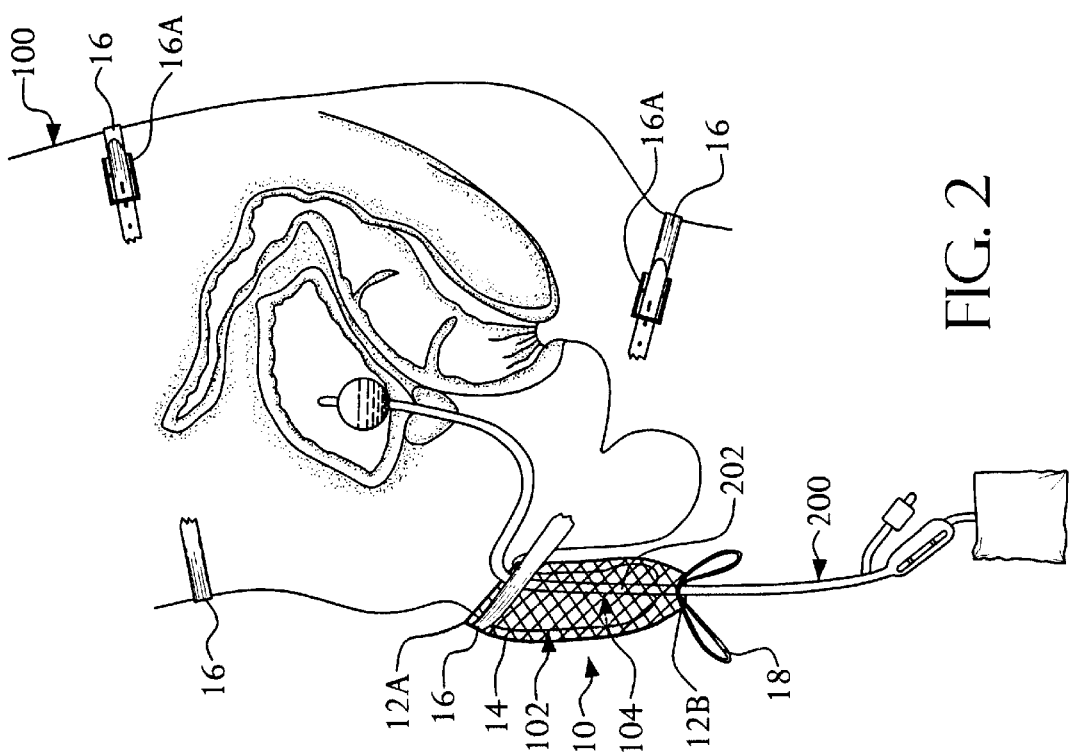
FIG. 2 is a side view of the device of the present invention in the non-constricted form attached to a patient illustrating the catheter.

Referring to FIG. 2, the device 10 is illustrated attached to a patient 100 wherein a catheter 200 has been inserted. The device 10 is attached to the patient by back loading the cylindrical body 12 over the penis 102. Thereafter, the strings 18 are tied and/or taped or otherwise fastened, and thereby secured to the catheter 200 at the distal end 12B of the cylindrical sleeve portion 12. The belts 16 at the proximal end 12A are secured to the patient's body 100 by buckles 16A attached thereto. The hook-and-pile fastener strap 20 (not illustrated in FIGS. 2 and 3 as it is hidden by the belt 16) encircles the proximal end 12A of the cylindrical sleeve portion 12 and is secured by complementary fastener ends 20A,B.

Figure 3:
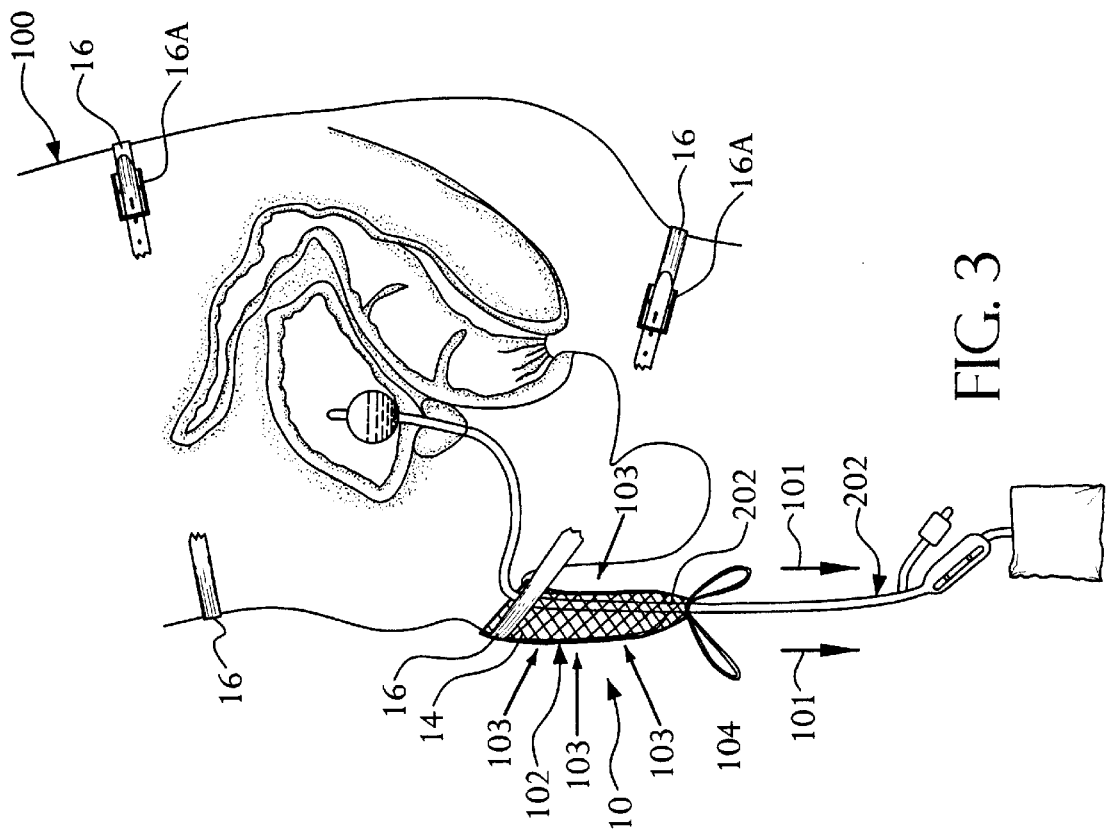
FIG. 3 is a side view of the device of the present invention in the constricted form attached to a patient illustrating the catheter.

Referring to FIG. 3, when force is asserted longitudinally (or outwardly) on the catheter 200, as shown by the vertical arrows 101 illustrating vertical movement with respect to the patient's body 100, the cylindrical sleeve portion 12, anchored by the ties 18, hook-and-pile fastener strap 20 and belts 16, elongates wherein the diagonal (and preferably helical) strands 14 react to the applied force, as shown by the horizontal arrows 103 illustrating substantially transverse movement constricting with respect to the patients body 100, reducing the diameter of the cylindrical sleeve portion 12. Specifically, the cylindrical sleeve portion 12 of the device 10 constricts around the penis 102, thereby reducing the diameter of the urethra 104 within the penis 102 of the patient 100, locking the catheter 202 therein from outward movement. The greater the amount of longitudinal force placed on the catheter 200, the greater the transverse constriction of the device 10 and therefore, the more secure the catheter 202 is maintained in position.

When the transverse force is discontinued, the cylindrical sleeve portion 12 returns to the relaxed configuration as best illustrated in FIG. 2, thereby increasing in diameter. Releasing the hook-and-pile fastener strap 20, belts 16 and strings 18 allows the device 10 to be removed as no constriction is possible without each end of the cylindrical sleeve portion 12 being anchored to the patient 100 and catheter 200.

The strands 14 forming the sleeve portion 12 of the device 10 are preferably diagonally woven as shown, but may be formed by other techniques, such as knitting or any other technique that will result in transverse or diametrical constriction of the cylindrical sleeve portion 12 when outward force is applied at the distal end 12B and resisted at the proximal end 12A.

I claim:

1. A male catheter securing device for use with an indwelling catheter having inflatable balloon that is inserted into the bladder of a male patient, which balloon has a drainage tube extending from the balloon, through and from the penis, for securing an indwelling catheter in place inside a patient and adapted for application about a penis comprising:
   a. a substantially cylindrical sleeve portion comprising strands having a proximal end and a distal end;
   b. a catheter securing means secured to said distal end for securing the device about a catheter drainage tube outside the penis; and
   c. a body securing means attached to said proximal end; wherein said sleeve portion comprises constricting means whereby, when force is applied to the distal end and that force is opposed at the proximal end so as to tend to stretch the sleeve portion longitudinally, the sleeve portion will constrict in the transverse direction to increasingly more tightly grip the penis as increasingly longitudinal forces are applied.

2. The male catheter securing device of claim 1, wherein said catheter securing means is at least a catheter drainage tube fastener for fastening said cylindrical sleeve portion to a catheter drainage tube.

3. The male catheter securing device of claim 2, wherein said body securing means is at least a body fastener for attaching said cylindrical sleeve portion to the body of a patient.

4. The male catheter securing device of claim 2, wherein said body securing means further includes a penis fastener for securing said cylindrical sleeve portion to the penile base.

5. The male catheter securing device of claim 1, wherein said strands are made of resilient substantially non-elastic material.

6. The male catheter securing device of claim 1, wherein the strands are helical.

7. The male catheter securing device of claim 1, wherein the strands are diagonal.

8. The male catheter securing device of claim 1, wherein the catheter securing means is a plurality of strings for tying said cylindrical sleeve portion to the catheter.

9. The male catheter securing device of claim 1, wherein the body securing means is a plurality of belts for tying said cylindrical sleeve portion to the body of a patient.

10. The male catheter securing device of claim 1, wherein the body securing means is a hook-and-pile fastener strap for attaching said cylindrical sleeve portion to the penile base.

11. The male catheter securing device of claim 1, wherein said catheter securing means for securing the device about a catheter drainage tube include tape means.

12. A male catheter securing device for use with an indwelling catheter having an inflatable balloon that is inserted into the bladder of a male patient, which balloon has a drainage tube extending from the balloon, through and from the penis, for securing an indwelling catheter in place inside a patient and adapted for application about a penis comprising:
   a. a substantially cylindrical sleeve portion comprising strands having a proximal end and a distal end;
   b. a catheter securing means secured to said distal end for securing the device about a catheter drainage tube outside the penis; and
   c. a body securing means attached to said proximal end; wherein said sleeve portion comprises constricting means whereby, when force is applied to the distal end and that force is opposed at the proximal end so as to tend to stretch the sleeve portion longitudinally, the sleeve portion will constrict in the transverse direction to increasingly more tightly grip the penis as increasingly longitudinal forces are applied,
   wherein said catheter securing means is a at least a catheter drainage tube fastener for fastening said cylindrical sleeve portion to a catheter drainage tube, wherein said catheter drainage tube fastener is a plurality of strings for tying said cylindrical sleeve portion to the catheter,
   wherein said body securing means is at least a body fastener for attaching said cylindrical sleeve portion to the body of a patient,
   wherein said body securing means further includes a penis fastener for securing said cylindrical sleeve portion to the penile base, wherein said penis fastener is a hook-and-pile fastener strap for attaching said cylindrical sleeve portion to the penile base,
   wherein said strands are made of resilient substantially non-elastic material, and
   wherein the strands are helical.

13. A male catheter securing device for use with an indwelling catheter having an inflatable balloon that is inserted into the bladder of a male patient, which balloon has a drainage tube extending from the balloon, through and from the penis, for securing an indwelling catheter in place inside a patient and adapted for application about a penis comprising:
   a. a substantially cylindrical sleeve portion comprising strands having a proximal end and a distal end;
   b. a catheter securing means secured to said distal end for securing the device about a catheter drainage tube outside the penis; and
   c. a body securing means attached to said proximal end; wherein said sleeve portion comprising constricting means whereby, when force is applied to the distal end and that force is opposed at the proximal end so as to tend to stretch the sleeve portion longitudinally, the sleeve portion will constrict in the transverse direction to increasingly more tightly grip the penis as increasingly longitudinal forces are applied,
   wherein said catheter securing means is a at least a catheter drainage tube fastener for fastening said cylindrical sleeve portion to a catheter drainage tube, wherein said catheter drainage tube fastener is a plurality of strings for tying said cylindrical sleeve portion to the catheter, wherein said body securing means is at least a body fastener for attaching said cylindrical sleeve portion to the body of a patient, wherein said body securing means further includes a penis fastener for securing said cylindrical sleeve portion to the penile base, wherein said penis fastener is a hook-and-pile fastener strap for attaching said cylindrical sleeve portion to the penile base, wherein said strands are made of resilient substantially non-elastic material, and wherein the strands are diagonal.

* * * * *